(12) United States Patent
König

(10) Patent No.: US 8,165,426 B2
(45) Date of Patent: Apr. 24, 2012

(54) WORKFLOW-BASED MANAGEMENT OF MEDICAL IMAGE DATA

(75) Inventor: Helmut König, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1480 days.

(21) Appl. No.: 11/700,145

(22) Filed: Jan. 31, 2007

(65) Prior Publication Data

US 2007/0192408 A1 Aug. 16, 2007

(30) Foreign Application Priority Data

Feb. 1, 2006 (DE) .......................... 10 2006 004 618

(51) Int. Cl.
*G06K 9/54* (2006.01)
*H04N 1/00* (2006.01)
(52) U.S. Cl. ..................... 382/305; 358/403; 358/434
(58) Field of Classification Search .................. None
See application file for complete search history.

(56) References Cited

U.S. PATENT DOCUMENTS

| | | | |
|---|---|---|---|
| 6,263,096 B1 * | 7/2001 | Boag et al. ................... | 382/128 |
| 6,683,933 B2 | 1/2004 | Saito et al. | |
| 6,762,763 B1 | 7/2004 | Migdal et al. | |
| 7,184,612 B2 * | 2/2007 | Naftali et al. ................ | 382/304 |
| 7,570,790 B2 * | 8/2009 | Tsujii et al. ................. | 382/128 |
| 2003/0156745 A1 | 8/2003 | Saito et al. | |
| 2004/0120561 A1 * | 6/2004 | Goto ............................. | 382/128 |
| 2004/0128164 A1 * | 7/2004 | DeJarnette et al. ............. | 705/2 |
| 2005/0041842 A1 * | 2/2005 | Frakes et al. .................. | 382/128 |
| 2008/0234571 A1 * | 9/2008 | Hay et al. ...................... | 600/425 |

FOREIGN PATENT DOCUMENTS

WO WO 01/03067 A1 1/2001

OTHER PUBLICATIONS

Bukhres et al., "COBRA-based Architecture for Image Workflow in a Large Consortium of Hospitals", IEEE Distributed Objects and Applications, INSPEC, 1999, pp. 1-10.*
Frank Susan, Kaufman Arie, Massive Volume Rendering on a Volume Visualization Cluster. (Technical Report, Stony Brook Uni, Apr. 26, 2004).
Engel, Sommer, Ertl, A Framework for Interactive Hardware-Accelerated Remote 3D-Visualization, Data Visualization 2000, Springer Computer Science. pp. 67-177, 291.
Bukhres, Omran; Hoang, Dong: "CORBA-Based Architecture for Image Workflow in a Large Consortium of Hospitals", 1999, IEEE Distributed Objects and Applications, S. 252-261, ISBN: 0-7695-0182-6, INSPEC: 6352767, DOI: 10.1109/D0A.1999.794040.

* cited by examiner

*Primary Examiner* — Randolph I Chu
(74) *Attorney, Agent, or Firm* — Harness, Dickey & Pierce, P.L.C.

(57) ABSTRACT

A method, an arrangement and a product are disclosed, where a multiplicity of nodes are provided which are designed for processing medical image data. Following determination of the specific workflow for processing the image data in at least one embodiment, local, relevant nodes are determined which have the functionality to execute the particular workflow. The image data are then split into image data subsets, on the basis of the workflow, and are forwarded in dedicated fashion to the relevant nodes for the purpose of processing.

20 Claims, 2 Drawing Sheets

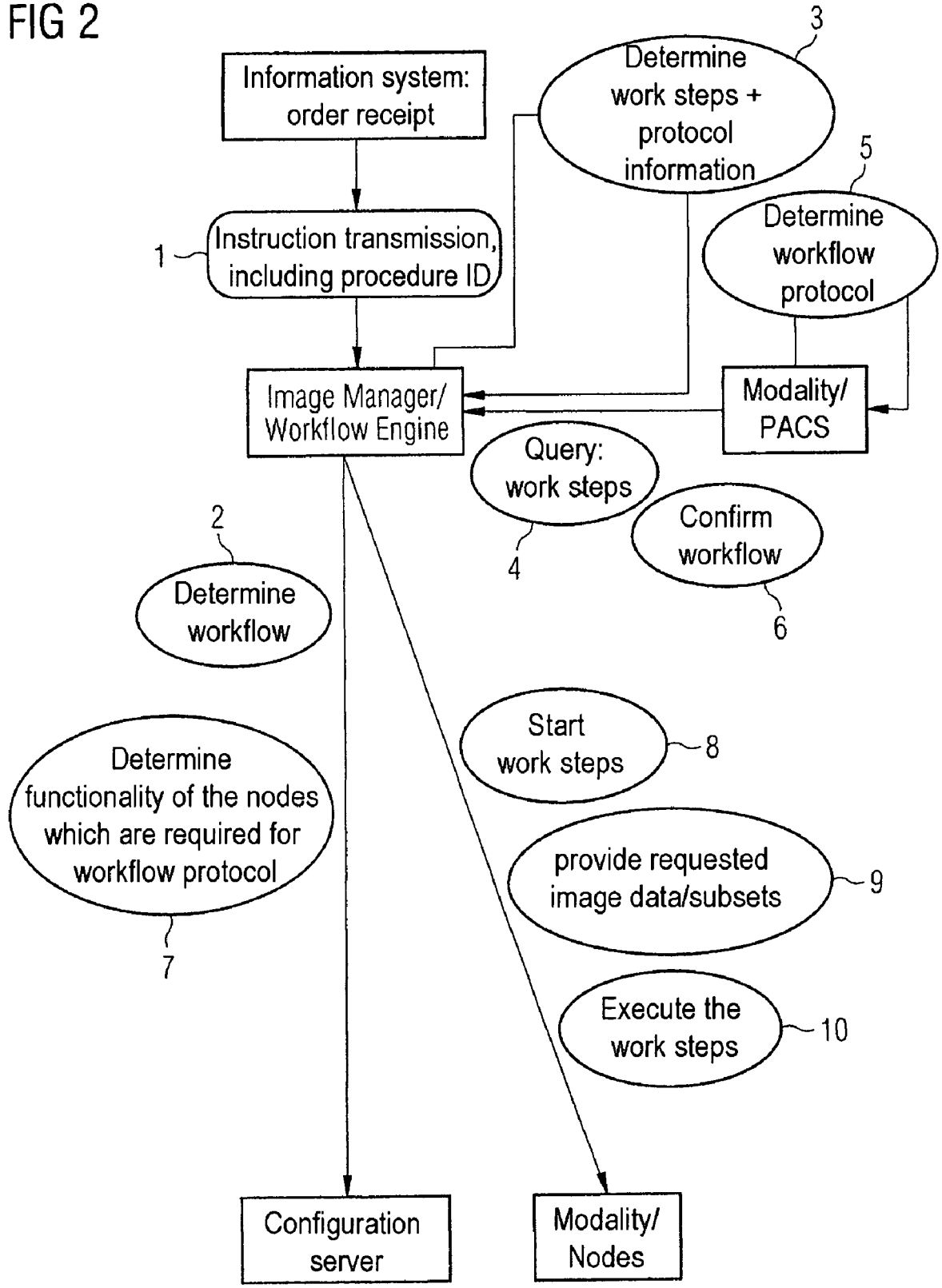

WORKFLOW-BASED MANAGEMENT OF MEDICAL IMAGE DATA

PRIORITY STATEMENT

The present application hereby claims priority under 35 U.S.C. §119 on German patent application number DE 10 2006 004 618.8 filed Feb. 1, 2006, the entire contents of which is hereby incorporated herein by reference.

FIELD

Embodiments of the invention generally relate to the field of data management of medical image data such as those, for example, which have been acquired at an arbitrary data source or imaging modality, such as on a computer tomograph, an NMR machine etc.

BACKGROUND

One problem of computer-aided imaging systems used today can be considered to be that an extremely large volume of data needs to be managed. The increased high-sensitivity and time resolution of the modalities used means that the number of image data items acquired there is continually rising, so that in sectional image diagnosis and in the case of multi-row CTs and functional NMR tomography, for example, the volume of data generated has continually increased in recent years. For certain examinations, this results in a data volume in the two-digit gigabyte range.

The significantly increased number of data items to be managed results in new problem scenarios in data management and when transmitting the data from the data source (that is to say the respective imaging modality) to one or more entities for the purpose of processing. Data system bottlenecks arise particularly when transmitting the image data via networks, e.g. via a WAN (wide area network) or via a LAN (local area network), and distributing them from the modality to analysis workstations and to the image archive, e.g. to a PACS system (picture archiving and communication system).

The increased volume of data means that the image data in a regular PACS environment can no longer readily be distributed to further entities or nodes in real time. The result is disadvantageously a "backlog", so to speak, at the data source, that is to say at the respective modality. This produces delays before the image data are available on the analysis workstation. In addition, delays arise before the image data can be safely archived on the modality following an acquisition. Previous systems are therefore found to be lacking and, in the worst case, there may even be a loss of data if the volume of data exceeds the available capacity.

To counteract the aforementioned problems, different approaches have been developed in the prior art to date.

Firstly, provision is made for some of the image data to be transmitted at different times when network load is low. Although this approach makes it possible to prevent the image data which are to be transmitted from being transported at peak network load times, it does not allow the data to be reduced and transmitted more quickly.

In addition, what is known as rule-based routing and prefetching of image data is known, where image data are purposefully sent to network nodes for further processing. In this context, purposeful sending is based on organizational structures, such as parameters relating to the department or the personnel, and on other organizational procedures, such as appointments, meetings etc.

In addition, approaches are known which provide image data compression and what is known as progressive loading. This approach involves compressed image data being transmitted at reduced resolution or in reduced quality. If required, further image data are subsequently loaded at a later time until the original resolution and the desired image quality has been achieved. Although this approach allows the volume of data to be reduced, the image data are not sent for purposeful distribution and association with particular nodes for the purpose of further processing.

Hence, this approach involves all of the image data, whether compressed or uncompressed, being sent to the relevant further processing nodes, when a subset of the data would sometimes have sufficed. When different examination data are repeatedly requested from analysis workstations, this approach results in a relatively high network load. Another drawback of this approach can be considered to be that in principle there is the risk of a loss of data, since a safe archiving option on the modality (in contrast to PACS archives) is normally not possible.

A further approach which may be cited from the prior art is the use of a central image processing server, in which central postprocessing (particularly rendering) of volume data records is carried out on a powerful image processing server, for which 3D graphic accelerators are normally used. An advantage of this approach can be considered to be that the requesting entity (the client) does not require the whole 3D data record, as would be the case for local calculation of the image display.

In this connection, reference can be made to the two American patent specifications U.S. Pat. No. 6,683,933 B2 and US 2003/0156745 A1, where provision is made for the data to be sent centrally to an image processing server or to an image manager (PACS). In the case of this method, the data volume for transmitting the rendered image data is significantly reduced.

A drawback of this approach is that the large volumes of data which are generated on the modalities must first of all be transmitted to a central node. The necessary full transmission of the large volumes of data to a central entity means that capacity bottlenecks often arise during transmission. Distribution of the data volumes over local nodes is not considered here.

SUMMARY

In at least one embodiment of the present invention, a way is demonstrated which allows the image data acquired at a data source to be distributed over different processing entities such that it is possible to reduce the volume of data which is to be transmitted and to achieve improved or even optimum matching to the respective workflow for processing the image data.

The description which follows describes embodiments of the invention on the basis of the inventive method.

The inventive solution, in at least one embodiment, relates particularly to a method for data management of medical image data, acquired at a data source, particularly a medical imaging modality, in a distributed environment having a plurality of processing nodes, which are computer-based, in particular, with the following method steps:

a data systems workflow for the image data is determined;
    relevant nodes from the set of fundamentally available
      nodes which have the functionality to be able to execute
      the determined workflow or to be able to execute individual steps in the determined workflow are determined;

the acquired image data are split into image data subsets using a splitting mechanism which is based on the selected workflow, and the image data subsets are purposefully forwarded or distributed to the relevant nodes for the purpose of processing.

Within the context of this document, the term "data management" is intended to be understood in a broad sense and covers all processes which can be included in the course of managing data. In particular, it relates to the purposeful or controlled routing of the data streams generated by the modality or data source to further entities for the purpose of further processing. The data management therefore covers the processing of data, particularly the postprocessing of image data, the storage and archiving of data, the transmission of data and the structuring of the data etc.

A data source is an appliance for generating or capturing digital data in medical engineering and particularly within the context of the imaging methods. Normally, these are known medical modalities which are used within the context of the imaging systems, such as computer tomographs, NMR machines etc. A fundamental concept of at least one embodiment of the present invention is not limited to these data sources or these appliances, however, and may likewise also be applied to other appliances for acquiring digital data, which do not necessarily have to be in the field of medical engineering.

The distributed environment is normally a network of any kind which connects together a plurality of computers, computer-aided appliances or other digital entities for processing data, particularly medical image data. Within the context of at least one embodiment of this invention, "nodes" are to be understood to mean all workstations or other entities which are equipped for processing the acquired image data. In this case, it is irrelevant whether the node is an intermediate node or a destination node. In the case of the intermediate node, the result of the processing of the intermediate node is forwarded to other nodes. The destination node is normally a memory unit, such as an image archive (e.g. the PACS system). Each node is fundamentally identified by a particular functionality.

One particular type of node is referred to as "relevant nodes". The relevant nodes are a subset of nodes which are characterized in that they are equipped with a particular functionality. The content of the "relevant nodes" is closely related to the respective workflow for the captured image data. In line with the invention, in at least one embodiment, the nodes are identified as being relevant to the respective image data which are required in order to be able to execute the particular workflow for handling the image data. By way of example, the following workflow may be determined for the captured image data: "Archive the captured image data". In this case, the nodes which have a functionality for archiving the image data are selected as being relevant. If appropriate, a plurality of relevant nodes can be determined. In this case, provision is made for a subsequent selection mechanism to take place in order to select the relevant nodes which, in relation to the respective instance of application, can be determined as the optimum node for executing the workflow. In this case, not only the functionality of the node but also other parameters may be included, such as the network utilization level for transmission to the node, the processor utilization level of the node, that is to say the load distribution etc.

An "image data subset" is a subset of the image data. A subset may therefore be any detail from the image data captured at the data source. The invention, in at least one embodiment, provides for the classification of the image data into image data subsets to be determined by the selected workflow. In other words, the image data are partitioned into image data subsets dynamically and in a different manner for each instance of application. The partitioning is based on the particular workflow.

The term "forwarding" the image data subsets to the relevant nodes is to be understood, in line with embodiments of the invention, to mean all the processes which are necessary in the course of distributing and transmitting the image data subsets. In an example embodiment, the captured image data are not forwarded as a complete packet to a central entity—as is done in the prior art—but rather are sent selectively and in a controlled fashion to local nodes. The term "forwarding" is therefore to be understood broadly and also relates to the sending and receiving of data using arbitrary protocols and arbitrary interfaces, with the data transmission being able to be initiated by the sender or by the receiver.

The invention, in at least one embodiment, makes it possible to ensure purposeful distribution of the original image data, of interim results and final results and of other evaluations to relevant nodes in the network. This advantageously makes it possible to reduce the data which is to be transmitted. In addition, the nodes involved are not overloaded with unnecessary "ballast data" which are not required for the respective processing. In line with the invention, only the image data subsets which are required for the processing at the node are sent to the respective node. Hence, the original image data are selectively forwarded to selected nodes.

In contrast to previous systems from the prior art, instead of using a central image processing server, at least one embodiment of the invention proposes a distributed solution in which the respective data source, that is to say the respective modality, sends the image data to the relevant nodes, to what are known as the image processing nodes, in parallel. The image data, namely the image data subsets, are preferably sent using a plurality of network cards, switches and/or other technical couplers.

One fundamental aspect of at least one embodiment of the present invention can be seen in that the image data are partitioned into image data subsets on the basis of the current and respective workflow. In principle, several options are provided for determining the workflow. This is normally done using a protocol. This is a succession of data systems work steps which need to be executed for a requested examination. In other words, it is a standardized procedure in which the individual work steps are executed on the basis of a scheme on different appliances, processors and/or systems. Normally, a particular workflow can be inferred merely on the basis of the type of image data captured and/or on the basis of the type of capture modality.

In an example embodiment of the present invention, a workflow is determined automatically on the basis of likewise captured parameters relating to the image data. The parameters may be the type of data source, the type of image data captured, the period of capture and/or other parameters. However, it is likewise possible for a user to define a particular workflow. By way of example, he can do this by selecting particular work steps from a set of possible work steps which is offered to him on a specific user interface.

In another, alternative embodiment of the invention, provision may be made for the workflow to be determined on the basis of an old, already executed workflow for another image project by simply adopting this workflow. The workflow (to be used synonymously with the term protocol) is therefore a succession of engineering-related work steps which are required for the data processing of the image data. These are not purely organizational structures.

Accordingly, a work step is identified by a process which is relevant within the context of the technical image data processing. A work step may thus be the setup and provision of a technical data transmission link, access to a specific data processing machine, archiving of data, various post-processing steps, compression methods for the image data, presentation or display of the image data etc.

In an example embodiment, a workflow is determined in relation to the image data captured from the data source. In one alternative embodiment, provision is made for the workflow to be determined in relation to the data source at which the image data are captured. In other embodiments, the workflow is determined on the basis of other parameters.

As soon as the workflow, including a succession of work steps, has been determined, the invention provides for the image data for the determined workflow to be split or partitioned. Following the partitioning, the result is a set of image data subsets. Normally, an image data subset relates to a work step within the context of the particular workflow. However, it is also possible for a plurality of image data subsets to be associated with a work step or for an image data subset to be associated with a plurality of work steps (this is the case particularly when a plurality of processing processes are intended to be carried out on the very same data).

In an example embodiment, the nodes are computer-aided appliances or machines or computers which execute defined work steps in the course of the data processing. The nodes are therefore part of a distributed computer architecture and, by way of example, may be workstations, databases, other archiving systems, memories, capture modalities, networks and/or network parts, management and/or administration entities etc. In the preferred embodiment, the nodes are therefore local nodes, each of which has an associated specific functionality. In one alternative embodiment, however, it is also possible for at least some nodes to be in the form of central nodes or for individual nodes to be combined to form one central node.

After, in line with at least one embodiment of the invention, the workflow for the image data has been determined and the image data have been split into image data subsets on the basis of the workflow, at least one embodiment of the invention provides for the image data subsets to be purposefully forwarded or sent to particular nodes which are respectively associated with them for the purpose of further processing. Hence, it is advantageously possible for the image data captured at a modality to be distributed and transmitted to local nodes on the basis of the respective requirement profile of the determined workflow. This allows better utilization of the capacity of the modality for storing further data by sending the captured data directly and automatically to other processing entities.

Normally, an image data subset is respectively transmitted separately or individually to its associated node. This allows a better load distribution to be achieved in the network. For performance reasons, one alternative embodiment provides for a plurality of image data subsets to be transmitted to a node in combination—so to speak in a packet.

A fundamental advantage of at least one embodiment of the inventive solution can therefore be considered as being that the split in the image data results in the respective image data subsets being sent in dedicated fashion to the nodes which have the requisite image processing functionality or the requisite services for the relevant image processing step (that is to say for the respective work step in the workflow).

In one advantageous, more complex development of an embodiment of the invention, the respective nodes are allocated the respective functionalities in a dynamic process. For each node, a previous phase in time is thus used to determine what services it can provide, or what functionality it needs to have, within the context of the medical image data processing. The capability or services is/are allocated to a node preferably on the basis of the particular workflow or the selected image processing protocol. This development allows the fundamental architecture or the fundamental design of the system to be matched flexibly to the current requirements. If, by way of example, there is a need to handle cases in which it is necessary for the image data captured at a modality to be merely archived then it will be appropriate for a plurality of nodes to be able to form an archiving functionality. Hence, the system can be adapted very variably and flexibly.

Normally, the image data subsets are forwarded to the respective relevant node using an association mechanism. The association mechanism is used to find, for an image data subset, the respective relevant node which is designed to carry out the respective work steps for the image data subset. If a plurality of nodes are suitable and hence are determined as relevant nodes, the association mechanism takes account of other parameters, so that it is possible to select a node and transmit the data to it. The other parameters will be aspects of the load balancing in the network, the status of the respective node (e.g. as far as the utilization level of the node is concerned) or other variables. In addition, the association mechanism is characterized by the possibility of performing prioritization for the nodes, so that there is a stipulation regarding the node to which the data are sent in a first step and the nodes to which they are sent in further steps.

To increase the flexibility of at least one embodiment of the inventive solution, provision is made for the splitting mechanism and/or the association mechanism to be able to be configured using a user interface at the system runtime too. This allows current requirements to be met.

In an example embodiment, the data source includes a temporary data store in which the acquired image data are stored and are accessible until safely archived. For safety reasons, data redundancy is consciously and purposefully provided here in order to be able to rule out any loss of data safely. In an alternative embodiment, the data source is not directly equipped with the temporary data store, but rather the temporary data store is indirectly connected to the data source. This can be done via a network or an appropriate network connection, for example.

In respect of requests for access to the image data from the data source, the invention provides for these requests sent to the data source to be rerouted. The requests are then respectively rerouted directly to the respective node at which the requested data are available. This allows the performance to be increased by decentralizing processing steps or work steps in the workflow. If the data which are to be accessed are available at a plurality of nodes then an access mechanism is provided which is used to decide the nodes to which the request is rerouted. This makes is possible to prevent unforeseeable performance losses from occurring at particular nodes, such as the data source. The access mechanism is preferably based on access to a configuration file. This configuration file stores priorities for access operations. The configuration file is usually associated with the image processing configuration server. Information both from an image manager and from a workflow engine goes into the configuration file.

The local splitting of the image data subsets allows the system to be utilized much better by sending the image data subsets to the respective relevant nodes in parallel.

Another way of achieving an inventive object, of at least one embodiment, is an arrangement for data management of medical image data, generated at a data source, in a distributed environment, having:

- a multiplicity of nodes with a specific functionality for executing data processing steps in relation to the captured image data,
- workflow determination means which are intended to determine an (image) data systems workflow for the captured image data,
- node determination means which are intended to determine relevant nodes from the set of fundamentally available nodes, where the relevant nodes have the functionality to be able to execute the workflow or to be able to execute individual workflow steps,
- at least one splitting module which is intended to split the image data into image data subsets, the splitting being based on the workflow determined by the workflow determination means, and
- at least one forwarding module which is intended for purposefully forwarding the image data subsets to the relevant nodes for the purpose of processing.

In addition, at least one embodiment of an inventive object is achieved by a system and an architecture for data management which are based on the method solution for at least one embodiment of the invention, described in detail above.

The inventive embodiments of at least one embodiment of the method which have been described above may also be in the form of a computer program product, where the computer is prompted to carry out at least one embodiment of the inventive method described above and its program code is executed by a processor.

One alternative way of achieving the object provides a storage medium which is intended to store the computer-implemented method described above and which can be read by a computer.

It is also possible for individual components of the method described above to be executed in one saleable unit and for the rest of the components to be executed in another saleable unit—so to speak as a distributed system. Another way in which at least one embodiment of the invention achieves the object is therefore a product for a data management system, comprising:

- a multiplicity of nodes with a specific functionality for executing data processing steps for the captured image data,
- workflow determination means,
- node determination means,
- at least one splitting module, and
- at least one forwarding module, where the product comprises means which are set up to carry out those steps in a method based on at least one of the method aspects described above which are brought about by the product, with at least one other product being set up to carry out the rest of the steps in the method, so that interaction between the two products carries out all of the steps in the method.

Further advantageous embodiments can be found in the subclaims.

BRIEF DESCRIPTION OF THE DRAWINGS

The detailed description of the figures which follows discusses example embodiments, which are to be understood as non-restrictive, and their features and other advantages with reference to the drawings, in which FIG. 2 shows an outlined illustration of a possible flow in line with an example embodiment of the invention.

DETAILED DESCRIPTION OF THE EXAMPLE EMBODIMENTS

Figure 1:
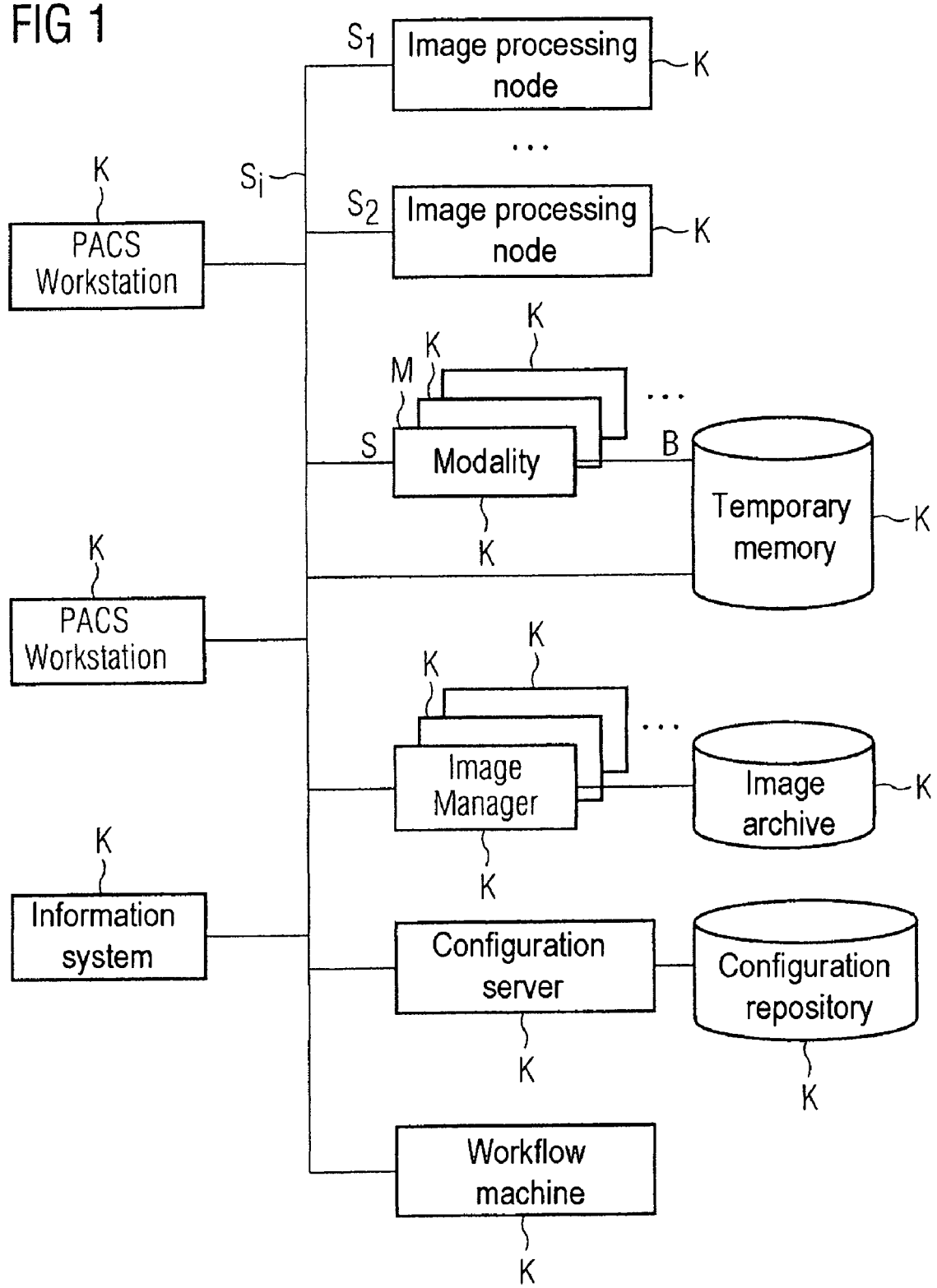
FIG. 1 shows an outlined illustration of the inventive architecture, including a multiplicity of different processing nodes in line with an example embodiment of the invention.

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

The text below describes the fundamental architecture of an embodiment of the inventive system in connection with FIG. 1.

An embodiment of the inventive system is designed for data management of medical image data B, such as X-ray images, CT images, tomograms from an NMR machine etc., generated at a data source, particularly at a modality M, in a distributed computer-aided environment having a multiplicity of nodes K.

The nodes K may be of different design and may have a respective different functionality. They are used for processing the image data B captured from the data source M. Examples of image processing nodes K which may be mentioned are: nodes for postprocessing of the data, an image manager, a configuration server for the image processing, a workflow machine or a workflow engine, an information system, PACS workstations, archives of different type or other repositories, e.g. a configuration repository for the configuration server. These nodes are shown in FIG. 1. In this context, it should be noted that FIG. 1 shows merely an exemplary selection of possible nodes, and these can be replaced or extended by any others in order to administrate, manage and/or process further the image data B captured at the modality M in any form.

Therefore, at least one node K will normally also be provided in order to subject the image data B automatically to configurable subsequent handling, such as postprocessing. Only the result of this subsequent handling will then be sent to the other local nodes. The type of subsequent handling is not limited and besides rendering, may include compression methods or other types of handling.

In line with an embodiment of the invention, the full image data B are not forwarded to a central entity for further processing, but rather the image data B which have been captured from a modality M are split, in line with a splitting mechanism, into a plurality of image data subsets S so that these can then be forwarded to the respective nodes K which are relevant to them.

In one example embodiment, the image processing nodes K are registered for particular image processing flows, for individual image processing steps and/or for image processing protocols via the image processing configuration server. Hence, provision is preferably made for the nodes to be registered for particular data system tasks in a preceding phase of the method. Each node K is allocated a particular task within the context of the workflow for image data processing. These may be typical postprocessing tasks, administration tasks, memory functions or other processes within the context of image processing.

In this case, a protocol is to be understood to mean a particular workflow for an image data record. The workflow usually includes a succession of individual work steps. In one advantageous development of an embodiment of the invention, provision is made for the allocation of particular functionalities within the context of the image processing to be able to be configured dynamically, too, for the respective nodes K. Hence, particular functionalities of a node K can also be changed if this is appropriate for the respective instance of application.

Following registration of the nodes K, it is also stipulated what node undertakes what tasks within the context of the image processing. In connection with the generation or capture of a particular image data subset, a particular workflow is now defined specifically for this image data record. This involves stipulating what work steps and in what order these are intended to be carried out on the image data.

FIG. 2 shows the above substantive matter in the oval identified by the digit "2". In FIG. 2, all actions are shown in an oval whereas the nodes K are shown as a rectangle.

In a further step, it is possible to split the image data which have been captured at the modality M into image data subsets S in line with a splitting mechanism. The split image data subsets S are then forwarded to the respective relevant nodes K for the purpose of processing.

The method which has just been presented relates to the basis method of an embodiment of the inventive solution. However, it is also possible to provide further method steps in a somewhat more complex development of an embodiment of the invention. This is shown in FIG. 2.

When an order for image data processing has been received, it is forwarded to the image manager or to the workflow engine in the course of the instruction transmission. This is identified in FIG. 2 by the action which is shown in the oval with the digit "1". Following instruction transmission, the image manager prompts determination of an appropriate image processing protocol. This can be done using a lookup table, for example. The image manager then makes the list of work steps in the work protocol available with further protocol information and can ask the respective modality M or the PACS workstation for an instruction work list and can acknowledge an instruction protocol after the modality M has selected an image processing protocol.

With these data and particularly with the succession of work steps which are to be executed, it is now possible for the image manager to select the image processing nodes K which have functionalities which are required for the respective work protocol. This can likewise be done by way of access to a lookup table and is sent to the configuration server for the image processing. The image manager can then prompt the acquisition and/or can execute the respective image processing work steps in a further phase, so that the necessary image data subsets S can be made available and so that the work steps can be executed sequentially or in parallel. The relevant data are forwarded to the modality M or to the respective image processing node K for this purpose.

Advantageously, provision is also made for rerouting requests for image processing data. In this connection, requests for access and/or for displaying image data and/or results of image data are sent from the respective client to the image manager or to the workflow engine and are rerouted from there to the relevant nodes K at which the data are available.

In one advantageous development of an embodiment of the invention, provision is made for the processing of three-dimensional or higher-dimensional image data preferably to involve just one image being transmitted which has been subjected to rendering. In this context, the client sends the parameters required for calculating the representation to the destination node K.

One important advantage of an embodiment of the inventive solution can be seen in that the respective work steps in the selected workflow can be executed either sequentially or in parallel if the workflow so allows. This achieves a significant increase in flexibility.

Another important advantage can be seen in that the performance of the modality M can be increased by virtue of access operations to the modality M being able to be rerouted to nodes K at which the respective data are available. Hence, prioritizable selective access to results of work steps is effected directly at the respective node K at which the data are stored, and no longer centrally on the modality M, which can therefore be relieved of access operations.

The configuration server for the image processing provides not only the image processing protocol, that is to say the respective workflow for the image processing, but also the functionalities and further information about the nodes K for flow control.

The image data B are—as already mentioned—divided into image data subsets S on the basis of the particular protocol and the work steps or protocol steps defined therein and are sent in dedicated fashion to intermediate nodes or destination nodes K which have the image processing capabilities required for the relevant image processing step or provide the required services. The image data subsets S, which can also be called chunks, may be a DICOM image series or adjacent slices of a volume data record, for example, whose anatomical association is identified by codes, e.g. using the DICOM "Primary Anatomic Structure Sequence" (0008, 228) for identifying the relevant image details ("specific anatomic structures of interest within the image"), the entire contents of which is hereby incorporated herein by reference.

Finally, it should be pointed out that the description of the invention and the example embodiments are, in principle, not to be understood to be restrictive in respect of a particular physical implementation of the invention. For a person skilled in the relevant art, it is obvious, in particular, that the invention can be partly or completely implemented in software and/or hardware and/or in a form distributed over a plurality of physical products—in this case particularly including computer program products.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for data management of medical image data, generated at a data source, in a distributed environment having a plurality of nodes including a processor, the method comprising:
    determining, by one of the plurality of nodes, a data systems workflow having a succession of work steps for the image data;
    determining, by one of the plurality of nodes, relevant nodes from the set of nodes which have the functionality to be able to execute the work steps;
    splitting, by one of the plurality of nodes, the image data into image data subsets, using a splitting mechanism, based on the selected workflow and each instance of an application using the workflow;
    forwarding, by one of the plurality of nodes, the image data subsets to the relevant nodes for processing; and
    rerouting, by at least one of the plurality of nodes, requests for the image data subsets to the relevant nodes.

2. The method as claimed in claim 1, wherein the node is respectively in the form of at least one of a central and a local node in the distributed environment.

3. The method as claimed in claim 1, wherein an image data subset is forwarded at least one of separately and together with other image data subsets to a node.

4. The method as claimed in claim 1, wherein the image data subsets are associated with the respective nodes determined to be relevant, taking into account the selected workflow.

5. The method as claimed in claim 1, wherein the image data subsets are forwarded to relevant nodes using an association mechanism.

6. The method as claimed in claim 5, wherein the association mechanism takes into account a functionality of at least one of the respective node, a load distribution between the nodes and other parameters.

7. The method as claimed in claim 1, wherein the image data generated or detected by the data source are temporarily buffer-stored in at least one of the data source and an entity associated therewith.

8. The method as claimed in claim 5, wherein at least one of the splitting mechanism and the association mechanism is configurable.

9. The method as claimed in claim 1, wherein the data source sends the image data subsets to the nodes in parallel for the purpose of at least one of forwarding and processing.

10. The method as claimed in claim 1, wherein requests for at least one of image data and image data subsets which are sent to the data source are rerouted to the respective node at which the requested at least one of image data and image data subsets are available.

11. The method as claimed in claim 1, wherein the functionalities are associated with the individual nodes at least one of dynamically and on the basis of the particular workflow.

12. A data management system to manage medical image data generated at a data source, the system comprising:
    a multiplicity of nodes with a specific functionality to execute data processing steps in the course of the medical image data management;
    workflow determination means for determining a workflow having a succession of work steps for the medical image data;

node determination means for determining relevant nodes from the set of nodes which have the functionality to be able to execute the work steps;

at least one splitting module to split the medical image data into image data subsets using a splitting mechanism, the splitting mechanism being based on the selected workflow and each instance of an application using the workflow;

at least one forwarding module to purposefully forward the image data subsets to the relevant nodes for processing; and at least one rerouting module to reroute requests for the image data subsets to the relevant nodes.

13. The system as claimed in claim 12, wherein a central workflow engine is connected in order to distribute the image data subsets and the local nodes.

14. A computer program loaded directly into a non-transitory memory in a computer and comprises software code sections which are used to execute the method steps as claimed in claim 1 when the program is running on a computer.

15. The method as claimed in claim 2, wherein an image data subset is forwarded at least one of separately and together with other image data subsets to a node.

16. The method as claimed in claim 2, wherein the image data subsets are associated with the respective nodes determined to be relevant, taking into account the selected workflow.

17. The method as claimed in claim 2, wherein the image data subsets are forwarded to relevant nodes using an association mechanism.

18. The method as claimed in claim 6, wherein at least one of the splitting mechanism and the association mechanism is configurable.

19. The method as claimed in claim 7, wherein at least one of the splitting mechanism and the association mechanism is configurable.

20. A non-transitory computer readable medium including program segments for, when executed on a computer device, causing the computer device to implement the method of claim 1.

* * * * *